United States Patent

Bøgesø et al.

[11] 4,136,193
[45] Jan. 23, 1979

[54] ANTI-DEPRESSIVE SUBSTITUTED 1-DIMETHYLAMINOPROPYL-1-PHENYL PHTHALANS

[75] Inventors: Klaus P. Bøgesø, Kgs. Lyngby; Anders S. Toft, Farum, both of Denmark

[73] Assignee: Kefalas A/S, Copenhagen-Valby, Denmark

[21] Appl. No.: 757,619

[22] Filed: Jan. 7, 1977

[30] Foreign Application Priority Data

Jan. 14, 1976 [GB] United Kingdom ............... 1486/76

[51] Int. Cl.² .............................................. A61K 31/34
[52] U.S. Cl. ............................... 424/285; 260/346.73
[58] Field of Search ................. 260/346.2 R; 424/285

[56] References Cited

U.S. PATENT DOCUMENTS 3,467,675   9/1969   Petersen et al. ............... 260/346.2 R

OTHER PUBLICATIONS

Petersen et al. (II), Acta Pharacol. Toxicol, 24 (2-3), pp. 121-133 (1966); Chem. Abst. vol. 65, 1966, 17531g.

Primary Examiner—Henry R. Jiles
Assistant Examiner—Bernard Dentz
Attorney, Agent, or Firm—Gordon W. Hueschen

[57] ABSTRACT

The present invention relates to phthalans of the following general formula:

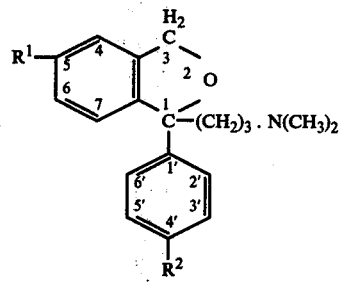

wherein $R^1$ and $R^2$ each represents halogen, a trifluoromethyl group, a cyano group or R—CO— wherein R is an alkyl-radical with from 1-4 C-atoms inclusive, as well as acid addition salts thereof with pharmaceutically acceptable acids.

18 Claims, No Drawings

ANTI-DEPRESSIVE SUBSTITUTED 1-DIMETHYLAMINOPROPYL-1-PHENYL PHTHALANS

It is an object of the present invention to provide phthalans of Formula I, a method of making the same, a method for the alleviation, palliation, mitigation, or inhibition of the manifestations of certain physiological-psychological abnormalities of animals therewith, and pharmaceutical compositions comprising such compounds as active ingredient.

Other objects will be apparent to one skilled in the art and still other objects will become apparent hereinafter.

BACKGROUND OF THE INVENTION

For many years, depressions were considered to be related to decreased activity of central adrenergic processes, and the antidepressant activity of imipramine-like drugs was suggested to result from an inhibition of noradrenaline re-uptake. Accordingly, the efforts concentrated on finding drugs which potentiated noradrenaline by preventing re-uptake. Among phthalans described in U.S. Pat. No. 2,467,675 it was found that the most potent compound having a noradrenaline potentiating effect was a phthalane having methyl groups in position 3 of the ring structure, no substituents in the phenyl ring, an unsubstituted phenyl ring in position 1, and a monomethylaminopropyl group attached to position 1. In fact, only compounds having two methyl groups at position 3 were found to be very potent potentiators of noradrenaline; P. V. Petersen et al.; Acta pharmacol. et toxicol. 1966, Vol. 24, pg. 121.

On the basis of recent advances in pharmacology and biochemistry of antidepressants and depressions, Carlsson et al.: "Effect of antidepressant drugs on the depletion of intraneuronal brain 5-hydroxytryptamine stores caused by 4-methyl-α-ethyl-meta-tyramine": Euro. J. Pharmacol., 1969, 5, pg. 357–366, suggested that blockade of 5-hydroxytryptamine re-uptake is involved in the mood-elevating action of tricyclic antidepressants, whereas blockade of noradrenaline re-uptake promotes drive in the depressed patients.

Also Lapin & Oxenkrug: "Intensification of the central serotoninergic processes as a possible determinant of the thymoleptic effect": Lancet, 1969, 1, pg. 132–136, suggest that the mood-elevating effect of monoamineoxidase inhibitors and of electroconvulsive therapy is related to an intensification of serotoninergic processes in the brain.

SUMMARY OF THE INVENTION

It has now surprisingly been found that the phthalans of Formula I as well as their acid addition salts with pharmaceutically acceptable acids have strong potentiating effects on tryptophan and 5-hydroxytryptophan as shown in standard reliable tests in vivo on test animals and also in vitro. At the same time the compounds have practically no potentiating effects on noradrenaline or adrenaline.

The compounds of Formula I, wherein at least one of the substituents $R^1$ and $R^2$ is a cyano group or, R—CO— are novel compounds, whereas the other compounds have been broadly claimed in U.S. Pat. No. 3,467,675 although they have not previously been prepared or suggested.

The compounds of Formula I and the non-toxic acid addition salts thereof may be administered both orally and parenterally, for example in the form of tablets, capsules, powders, syrups or solutions for injection.

The methods for the preparation of the phthalans of Formula I may be the methods wellknown in the art for the preparation of similar phthalans such as the methods described in U.S. Pat No. 3,467,675 or any obvious chemical equivalent of these methods.

According to the invention a method for the preparation of compounds of Formula I consists in the reaction of a compound of the following formula:

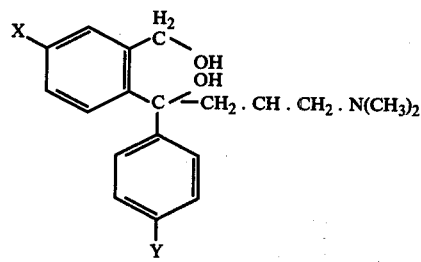

wherein X and Y each represents halogen or a trifluoromethyl group with a dehydrating agent, and isolating the compound of Formula I formed by the reaction as the free amine or an acid addition salt in conventional manner, and in the case when X or Y or both represent bromine, if desired, reacting the compound of Formula I with cuprous cyanide in an inert organic solvent and isolating the compound of Formula I wherein $R^1$ or $R^2$ each or both are a cyano group as the free amine or an acid addition salt in conventional manner.

The dehydration according to the invention may be effected by means of agents ordinarily used for dehydration purposes, e.g. concentrated hydrochloric acid, possibly mixed with glacial acetic acid, a phosphoric acid, a hydrogen halide, e.g. hydrogen chloride, in an inert organic solvent such as chloroform, benzene, toluene or the like. It is preferable to use weak to moderately strong acidic dehydrating agents and avoid very strong dehydrating agents such as concentrated sulphuric acid, as, otherwise, the dehydration of the compounds of Formula II may lead to undesired derivatives as described in British Pat. No. 939,856.

The acid addition salts of the compounds of Formula I are preferably salts of pharmacologically acceptable non-toxic acids such as mineral acids, for example, hydrochloride acid, hydrobromic acid, phosphoric acid, sulphuric acid, and the like, and organic acids such as acetic acid, tartaric acid, maleic acid, citric acid, oxalic acid, benzoic acid, methane sulphonic acid, embonic acid, and the like.

The starting dihydroxy compounds of Formula II may conveniently be prepared by reacting a compound of the following formula:

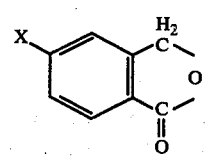

wherein X is as defined above, with a Grignard compound of the following formula:

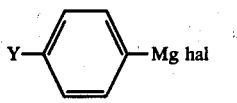

wherein Y is as defined above, and hydrolysing the reaction mixture with an acidic solution, isolating the resulting compound of the general formula:

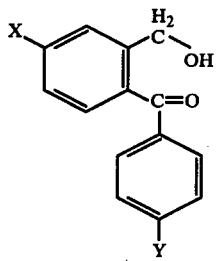

and reacting this compound with a N,N-dimethyl propyl magnesium halide in an ether such as diethylether or tetrahydrofuran and isolating the resulting dihydroxy compound of Formula II.

The compounds of Formula I may also be prepared by reacting a compound of the general formula:

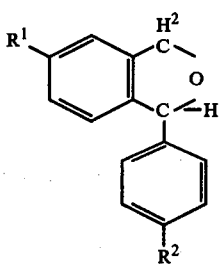

wherein $R^1$ and $R^2$ are as defined above with a 3-dimethylaminopropyl halide, in the presence of a condensing agent such as an alkali amide, for example sodamide or potassium amide, butyllithium, phenyllithium or the like, and isolating the compound of Formula I obtained either as the free amine or as a non-toxic acid addition salt. The reaction is preferably carried out in the presence of an inert organic solvent. When compounds of Formula I, wherein at least one of $R^1$ and $R^2$ is R.CO, are desired, it has — according to the invention — in some cases been found advantageous to prepare such compounds by reacting a compound of the formula:

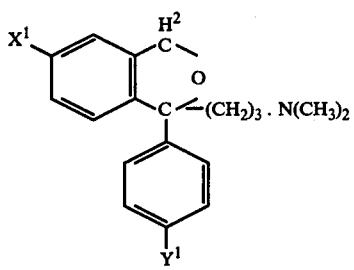

wherein $X^1$ and $Y^1$ each represents halogen, a trifluoromethyl group or a cyano group, at least one of $X^1$ and $Y^1$ being a cyano group, with an alkyl magnesium halide of the formula RMghal, wherein R is as previously defined, hydrolysing the magnesium complex formed by the reaction, and isolating the compound of Formula I as the free amine or as an acid addition salt thereof in conventional manner.

The Grignard reaction is carried out in conventional manner in an inert organic solvent such as diethyl ether or tetrahydrofuran.

The following examples are given by way of illustration only and are not to be construed as limiting.

EXAMPLE 1

1-(4'-chlorophenyl)-1-(3-dimethylaminopropyl-5-bromophthalan and its oxalate.

The starting material, (4-bromo-2-(hydroxymethyl)-phenyl)-(4-chlorophenyl)-(3-dimethylaminopropyl)methanol was prepared in the following manner:

A Grignard-solution prepared from 220 grams (1.15 mol) of p-chlorobromobenzene and 29 grams of magnesium turnings (1.2 mol) in 1500 milliliters of dry ether was added dropwise in the course of one hour to a suspension of 213 grams of 5-bromphthalide (1 mol) in 1500 milliliters of dry tetrahydrofuran. The temperature was not allowed to rise over 10 degrees Centigrade. After the addition was completed the reaction mixture was stirred for three hours at room temperature. The mixture was then poured into 2 liters of icewater and 100 milliliters of saturated aqueous ammonium chloride were added. The etherphase was separated and the water-tetrahydrofuranphase extracted once with 500 milliliters of ether. The etherphase was washed with water, dried over anhydrous magnesiumsulphate, filtered and evaporated in vacuum to yield 320 grams of 2-hydroxymethyl-4-bromo-4'-chloro-benzophenone in the form of a yellow oil which was not purified further but used directly in the next step. The 320 grams of oil were dissolved in 200 milliliters of dry tetrahydrofuran and added dropwise to a great excess of N,N-dimethylaminopropyl magnesium chloride in tetrahydrofuran under gentle reflux. After completed addition the mixture was refluxed over night. The reaction mixture was then poured into 5 liters of icewater and 200 milliliters of saturated aqueous ammonium chloride solution added. The mixture was extracted with a total of 2500 milliliters of ether. The etherphase was then extracted with 20% aqueous acetic acid to acid reaction, whereupon the acetic acid solution was made alkaline with 10 N sodiumhydroxide solution. After cooling, the oil, which separated out, was extracted twice with 500 milliliters of ether. The combined ether extracts were dried over anhydrous potassium carbonate, treated with active carbon and evaporated in vacuum. The remaining oil consists of somewhat impure (4-bromo-2-(hydroxymethyl)phenyl)-(4-chlorophenyl)-(3-dimethylaminopropyl)methanol which was used in the next step without further purification. Yield: 219 grams.

The 218 grams of oil from the previous step were heated for three hours on a steam bath with 1800 milliliters of 60% aqueous phosphoric acid while stirring vigorously. The reaction mixture was neutralized with saturated aqueous ammonia while continuously adding ice. The reaction mixture was then extracted with 1500 milliliters of ether, the etherphase separated, dried over anhydrous potassium carbonate, treated with active carbon and evaporated in vacuum. The residue was distilled in vacuum and 105 grams of 1-(4'-chlorophenyl)-1-(3-dimethylaminopropyl)-5-bromophthalan was obtained as an oil which boiled at 188–190 degrees Centigrade/0.1mm Hg.

The corresponding oxalate was prepared in conventional manner from ethanol and melted at 178–180 degrees Centigrade.

In similar manner were prepared the following compounds of Formula I from the appropriate compounds of Formula II:

1-(4'-fluorophenyl)-1-(3-dimethylaminopropyl)-5-bromophthalane, B.P. 174 degrees Centigrade/0.1mm Hg, the corresponding oxalate melts at 148–150 degrees Centigrade.

1-(4'-chlorophenyl)-1-(3-dimethylaminopropyl)-5-chlorophthalane, its oxalate which melts at 180–182 degrees Centigrade and its hydrobromide which melts at 136–142 degrees Centigrade.

1-(4'-bromophenyl)-1-(3-dimethylaminopropyl)-5-chlorophthalane; B.P. 185 degrees Centigrade/0.08mm Hg.

1-(4'-fluorophenyl)-1-(3-dimethylaminopropyl)-5-chlorophthalane; B.P. 160–164 degrees Centigrade/0.05mm Hg, its oxalate which melts at 152–155 degrees Centigrade and its hydrochloride which melts at 168–171 degrees Centigrade.

1-(4'-chlorophenyl)-1-(3-dimethylaminopropyl)-5-trifluoromethyl-phthalane and its oxalate which melts at 184–186 degrees Centigrade.

1-(4'-bromophenyl)-1-(3-dimethylaminopropyl)-5-trifluoromethyl-phthalane; B.P. 162 degrees Centigrade/0.2mg Hg and its oxalate which melts at 190–193 degrees Centigrade.

1-(4'-fluorophenyl)-1-(3-dimethylaminopropyl)-5-trifluoromethyl-phthalane, its oxalate which melts at 141–147 degrees Centigrade, and its hydrochloride which melts at 159–161 degrees Centigrade.

1-(4'-fluorophenyl)-1-(3-dimethylaminopropyl)-5-fluorophthalane; B.P. 140 degrees Centigrade/0.02 mm Hg, and its hydrochloride which melts at 172–174 degrees Centigrade.

1-(4'-chlorophenyl)-1-(3-dimethylaminopropyl)-5-fluorophthalane; B.P. 161 degrees Centigrade/0.02 mm Hg, and its oxalate which melts at 155–157 degrees Centigrade.

EXAMPLE 2

1-(4'-chlorophenyl)-1-(3-dimethylaminopropyl)-5-phthalancarbonitrile, and its hydrobromide.

105 grams of 1-(4'-chlorophenyl)-1-(3-dimethylaminopropyl)-5-bromophthalane and 28 grams of cupro-cyanide were refluxed for four hours in 75 milliliters of dimethylformamide. While still warm the reaction mixture was poured into a solution of 55 milliliters of ethylenediamine in 165 milliliters of water. The mixture was shaken vigorously and the blue colored aqueous phase was decanted from the oily base. The aqueous phase was extracted once with 200 milliliters of benzene and the benzene phase added to the oily base. The collected organic phase was washed with 10% aqueous sodiumcyanide solution and water, dried over anhydrous sodium sulphate, treated with active carbon and evaporated. The resulting oil was dissolved in ether and extracted with 20% aqueous acetic acid. The acetic acid solution was made alkaline with 10N aqueous sodium hydroxide solution and extracted with ether. The ether phase was separated, dried over anhydrous potassium carbonate, treated with active carbon and evaporated in vacuum. Yield: 76 grams of 1-(4'-chlorophenyl)-1-(3-dimethylaminopropyl)-5-phthalancarbonitrile. The hydrobromide was prepared in conventional manner and crystallizes from isopropylalcohol and melts at 148–150 degrees Centigrade.

In equivalent manner were prepared:

1-(4'-fluorophenyl)-1-(3-dimethylaminopropyl)-5-phthalancarbonitrile; B.P. 175 degrees Centigrade/0.03 mm Hg, its oxalate which melts at 164–166 degrees Centigrade, and its hydrobromide which melts at 182–183 degrees Centigrade.

1-(4'-cyanophenyl)-1-(3-dimethylaminopropyl)-5-phthalancarbonitrile and its hydrochloride which melts at 167–169 degrees Centigrade.

1-(4'-cyanophenyl)-1-(3-dimethylaminopropyl)-5-chlorophthalane and its oxalate which melts at 187–191 degrees Centigrade.

1-(4'-cyanophenyl)-1-(3-dimethylaminopropyl)-5-trifluoromethylphthalane and its oxalate which melts at 189–192 degrees Centigrade.

EXAMPLE 3

1-(4'-fluorophenyl)-1-(3-dimethylaminopropyl)-5-phthalancarbonitrile and its oxalate.

The starting material, 1-(4'-fluorophenyl)-5-cyanophthalane, was prepared in the following manner:

300 grams of 4-bromo-4'-fluoro-2-(hydroxymethyl)-benzophenone were dissolved in 750 milliliters of ether and added dropwise to a suspension of 25 grams of lithium aluminium hydride in 900 milliliters of ether at such speed that the mixture refluxed gently. Then the mixture was refluxed for two hours, whereupon it was hydrolysed with water. The etherphase was decanted from the precipitated metal salts which were washed twice with ether. The collected ether phases were dried over anhydrous magnesium sulphate and evaporated in vacuum. Yield: 305 grams of impure (4-bromo-2-(hydroxymethyl)phenyl)-(4-fluorophenyl)methanol in the form of an oil, which was used directly in the next step.

The 305 grams of oil were heated for three hours on a steam bath in 2400 milliliters of 60% aqueous phosphoric acid while stirring vigorously. The mixture was poured into two liters of icewater and extracted with ether. The ether phase was washed to neutral reaction with water and dried over anhydrous magnesium sulphate, treated with active carbon and evaporated in vacuum. The residue (256 grams) was distilled in vacuum and 177 grams of 1-(4'-fluorophenyl)-5-bromophthalane boiling at 170–175 degrees Centigrade/1 mm Hg was obtained as a yellow oil.

177 grams of 1-(4'-fluorophenyl)-5-bromophthalane and 62.5 grams of cupro cyanide were refluxed for four hours in 200 milliliters of dimethylformamide. The reaction mixture was poured out in a solution of 120 grams of of sodium cyanide in 600 milliliters of water. The mixture was stirred for ten minutes and cooled. The crystals which separated out were sucked off and the filtrate extracted once with 200 milliliters of benzene. The crystals were dissolved in 200 milliliters of benzene and the combined benzene phases extracted with 10% aqueous sodium cyanide solution and water, dried over anhydrous magnesium sulphate, treated with active carbon and evaporated in vacuum. Upon cooling 1-(4'-fluorophenyl)-5-phthalancarbonitrile crystallizes; petroleum ether was added and the crystals sucked off. Yield: 122 grams, which melted at 87–90 degrees Centigrade. Upon recrystallization from ether and petroleum ether (1:1) there was obtained 96 grams melting at 95–97 degrees Centigrade.

21 grams of sodium hydride (50% in mineral oil) were dissolved in a nitrogen atmosphere in 900 milliliters of dimethyl sulfoxide at 60–70 degrees Centigrade. To the resulting sodium methylsulfinylmethid solution were added dropwise while cooling 96 grams of 1-(4'-fluorophenyl)-5-phthalancarbonitrile dissolved in 150 milliliters of dimethylsulfoxide. The reaction temperature was kept at 25 degrees Centigrade. When the addition was completed the mixture was stirred for ten minutes at room temperature. Thereupon, 53 grams of 3-dimethylaminopropyl chloride in 25 milliliters of dimethylsulfoxide were added quickly, and the reaction mixture was heated to 40 degrees Centigrade and kept there for 50 minutes. Then the mixture was poured into icewater and extracted with ether. The ether phase was extracted 20% aqueous acetic acid. The acetic acid solution was made alkaline with 10N sodium hydroxide solution and extracted with ether which was washed several times with water. The ether phase was separated, dried over anhydrous potassium carbonate, treated with active carbon and evaporated in vacuum. The residue was an oil (80 grams) which was distilled in vacuum and yielded 56 grams of 1-(4'-fluorophenyl)-1-(3-dimethylaminopropyl)-5-phthalancarbonitrile which boiled at 175–181 degrees Centigrade/0.03 mm Hg.

The corresponding oxalate was obtained in conventional manner from ethanol and melted at 163–166 degrees Centigrade. The hydrobromide melts at 182–183 degrees Centigrade.

In corresponding manner was prepared:
1-(4'-chlorophenyl)-1-(3-dimethylaminopropyl)-5ionylphthalane and its oxalate, which melts at 134–139 degrees Centigrade.

Example 4

1-(4-(chlorophenyl)-1-(3-dimethylaminopropyl)-5-propionylphthalane and its oxalate.

A solution of 1-(4-chlorophenyl)-1(3-dimethylaminoprol)-5-phthalancarbonitrile (23 grams, 0.068 mole) in 100 milliliters of dry benzene was added to ethyl magnesium bromide (prepared from 20 grams of ethylbromide and 4.8 grams of magnesium turnings in 100 milliliters of diethyl ether). The ether was distilled from the reaction mixture until the temperature reached 70 degrees Centigrade, whereupon the resulting mixture was refluxed overnight. The mixture was then poured into an ice cold aqueous solution of ammonium chloride and extracted with ether. The organic phase was extracted with 4 N hydrochloric acid and the extract heated for two hours on a steambath. After cooling, the solution was made alkaline, extracted with ether, washed with water, dried and evaporated to afford 18 grams of 1-(4-chlorophenyl)-1-(3-dimethylaminopropyl)-5-propionylphthalane as an oil.

The oxalate, which melted at 134–139 degrees Centigrade, was obtained by crystallization from methylisobutylketone.

The compounds of Formula I and the non-toxic acid addition salts thereof may be administered both orally and parenterally and may be used for example in the form of tablets, capsules, powders, syrups or in the form of the usual sterile solutions for injection. Results upon administration have been gratifying.

Most conveniently the compounds of Formula I and the non-toxic acid addition salts thereof are administered orally in unit dosage form such as tablets or capsules, each dosage unit containing one of the said compounds in an amount of from about 0.1 to about 50 milligrams, most preferably, however, from about 0.5–25 mg, calculated as the free amine, the total daily dosage usually ranging from about 0.5 to about 300 mg. The exact individual dosages as well as daily dosages in a particular case will, of course, be determined according to established medical principles.

When preparing tablets, the active ingredient is for the most part mixed with ordinary tablet adjuvants such as corn starch, potato starch, talcum, magnesium stearate, gelatine, lactose, gums, or the like. A suitable formula for a tablet containing 10 mg of 1-(4'-fluorophenyl)-1-(3-dimethylaminopropyl)-5-phthalancarbonitrile (called Lu 10-171) for short) in the form of its hydrochloride is as follows:

| | | |
|---|---|---|
| Lu 10-171, hydrochloride | 11.2 | mg |
| Potato starch | 36 | mg |
| Lactose | 18 | mg |
| Gelatine | 5 | mg |
| Talcum | 6 | mg |
| Magnesium stearate | 0.4 | mg |

Any other pharmaceutical tableting adjuvants may be used provided they are compatible with the active ingredient, and additional compositions and dosage forms may be similar to those presently used for thymoleptics such as imipramine, amitriptyline or nartriptyline. Also combination of the compounds of Formula I as well as their non-toxic acid addition salts with other active ingredients, especially other thymoleptics, neuroleptics or the like fall within the scope of the present invention.

As previously stated, when isolating the compounds of Formula I in the form of an acid addition salt, the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethanesulphonates, lactates, citrates, tartrates or bitartrates, and maleates of the amines of Formula I. Other acids are likewise suitable and may be employed, if desired. For example fumaric, benzoic, ascorbic, succinic, salicylic, bismethylenesalicylic, propionic, gluconic, malic, malonic, mandelic, cannamic, citraconic, embonic, stearic, palmitic, itaconic, glycolic, benzenesulphonic, and sulphamic acids may also be employed as acid addition saltforming acids. When it is desired to isolate a compound of the invention in the form of the free base, this may be done according to conventional procedure, as by dissolving the isolated or unisolated salt in water, treating with a suitable alkaline material, extracting the liberated free base with a suitable organic solvent, drying the liberated free base with a suitable organic solvent, drying the extract and evaporating to dryness or fractionally distilling to effect isolation of the free basic amine.

It is to be understood that the invention is not limited to the exact details of operation or exact compound or compositions shown and described as obvious modifications and equivalents will be apparent to one skilled in the art.

The phthalanes of Formula I as well as their non-toxic acid addition salts have been tested for their ability to potentiate 5-hydroxytryptophan and tryptophan with standard reliable test methods. In the testing they have been compared with known antidepressants.
5-hydroxytryptophan potentiation The 5-hydroxytryptophan potentiation test was performed essentially as described by Carlsson et al.: "Brain Research" 12. 456–460, 1969. The test substance was given intraperitoneally 30 minutes before intravenous administration of 5-hydroxytryptophan, 100 mg/kg in mice. An unpretreated group served as control. After this dose of 5-hydroxytryptophan the control animals remain unaffected. If the animals have been pretreated with a substance which inhibits the re-uptake of 5-hydroxytryptamine, a characteristic syndrome will occur. This consists of the following symptoms: (1) excitation, (2) tremor, and (3) abduction of the hind limbs. Each animal was given one point for each symptom present within a 15 minute observation period, and ED50 was defined as the dose that provoked a score half that of maximal obtainable score.

Tryptophan potentiation

The tryptophan potentiation test was performed as described above, except that tryptophan (100 mg/kg i.v.) was used instead of 5-hydroxytryptophan and that the mice were pretreated with nialamide (100 mg/kg p.o.), 18–20 hours before testing.

Inhibition of $^{14}$C-5-HT-uptake in rabbit blood platelets in vitro

The method is a slight modification of that described by Lingjaerde in Psychopharmacologia 17, 94–99, 1970. Two ml of rabbit platelet-enriched plasma, containing EDTA as an anticoagulant, were incubated with test compound and 2 ml of 0.05 M Na-P-buffer, pH 7.2, for 5 minutes at 37° C. Hereafter, $^{14}$C-5-HT (final conc. 120 nM) was added, and the incubation was continued for 15 minutes. The incubation was terminated by transferring the test tubes to an ice bath, and the platelets were isolated by centrifugation (~4000 g, 5 min., 4° C.). After draining, the platelets were gently washed with 4 ml of ice-cold saline, and the remaining radioactivity was determined. The uptake in the test samples was calculated in percent of the uptake in the control group and plotted against the concentration of test compound on semilogarithmic probability paper, from which the IC50-value was determined.

Inhibition of the H 75/12-induced depletion of 5-HT in rat brain in vivo

This was studied by a modification of the method developed by Carlsson and coworkers in Eur.J.Pharmacol. 5, 357–366, 1969. By this method depletion of 5-HT caused by H 75/12 (4-methyl-α-ethyl-meta-tyramine) could be prevented by thymoleptic drugs by inhibiting the uptake of H 75/12 into 5-HT-neurons.

Drugs (in saline, 10 ml/kg) were given s.c. After 20 min. an intraperitoneal injection of H 75/12 (50 mg/kg, 10 ml/kg) was given. Two hours after this injection the animals were killed by a blow to the head. 5-HT in the brain was determined fluorimetrically according to Anden and Magnusson; Acto Physiol. Scand., 69, 87–94, 1967.

The brains of rats receiving drug plus H 75/12 was always compared with rats receiving H 75/12 alone or vehicle alone.

Log dose-response curves were calculated by linear regression-analysis, and the dose (ED25) causing a 25 percent reduction of the depletion was determined.

Inhibition of $^3$H-NA uptake in mouse atria in vitro

For measuring the inhibition of uptake of $^3$H-NA (tritiated noradrenaline) in mouse atria in vitro a modification of the method described by Sachs in Acta Physiol. Scan. Suppl. 341, 1–67, 1970, and by Jonsson & Sachs in Eur.J.Pharmac. 16, 55–62, 1971, was used. The atria were preincubated with drugs for 5 min. at 37° C. in oxygenated Krebs-Ringer phosphate-buffer, pH 7.4. Thereafter, $^3$H-NA (final cons. $10^{-7}$ M) was added, and the incubation was continued for 15 minutes. Extra-cellular and loosely bound $^3$H-NA washed out in isotope free buffer for 10 minutes. The remaining radioactivity was determined, and the uptake was calculated as percent of uptake in a control group. IC50's (concentrations necessary to effect 50% inhibition in the tests conducted) were determined from log. concentration-response curves.

The results obtained will appear from the following table where chlorimipramine, imipramine, desipramine, amitriptyline and nortriptyline, all wellknown thymoleptics, have been used as reference substances.

| Codename | $R^1$ | $R^2$ | Tryptophan pot. ED$_{50}$ mg/kg i.p. | 5HTP pot. ED$_{50}$ mg/kg i.p. | C$_{14}$ 5-HT uptake inhibitory concentration IC$_{50}$ × 10$^7$N | H75/12 test ED$_{50}$ mg/kg | 3H-Na uptake in vitro IC$_{50}$ × 10$^9$M |
|---|---|---|---|---|---|---|---|
| Lu 10-199 | Cl | Cl | 1.6 | 2.1 | 0.20 | 0.53 | 16000 |
| Lu 9-199 | Cl | F | 1.9 | 4.1 | 0.21 | 0.18 | >10000 |
| Lu 9-269 | Cl | CF$_3$ | 1.6 | 6.1 | 1.40 | | |
| Lu 10-059 | Cl | CN | 0.8 | 1.9 | 0.29 | 1.40 | |
| Lu 10-162 | Br | Cl | 4.6 | 5.4 | 0.22 | 0.34 | 49000 |
| Lu 10-132 | Br | F | 3.4 | 2.7 | 0.31 | 0.65 | 22000 |
| Lu 12-007 | CF$_3$ | Cl | 0.8 | 1.2 | | | |
| Lu 12-012 | CF$_3$ | F | 1.2 | 2.8 | | | |
| Lu 10-047 | CF$_3$ | CN | 2.3 | 2.6 | 0.29 | 1.1 | 27000 |
| Lu 10-202 | CN | Cl | 0.8 | 0.9 | 0.17 | 0.18 | 23000 |
| Lu 10-171 | CN | F | 0.9 | 2.3 | 0.14 | 0.27 | 36000 |
| Lu 10-042 | CN | CN | 0.4 | 1.2 | 0.29 | 0.31 | >10000 |
| Lu 10-196 | C$_2$H$_5$CO | Cl | 3.4 | 2.7 | 0.15 | | 11000 |
| Lu 12-166 | F | F | 1.8 | 1.3 | 0.34 | 0.58 | 13000 |
| Lu 12-168 | F | Cl | 7.2 | 3.1 | 0.16 | 0.36 | 13000 |
| Chlorimipramine | | | 2.6 | 3.9 | 0.77 | 0.80 | 270 |
| Imipramine | | | 9.4 | 13 | 3.9 | 7.5 | 75 |
| Desipramine | | | >20 | >20 | 34 | 35 | 1.4 |
| Amitriptyline | | | >20 | 21 | 5.0 | 54 | 130 |
| Nortriptyline | | | >20 | >20 | 33 | 14 | 29 |

We claim:

1. A compound selected from the group consisting of (1) a phthalane of the general formula:

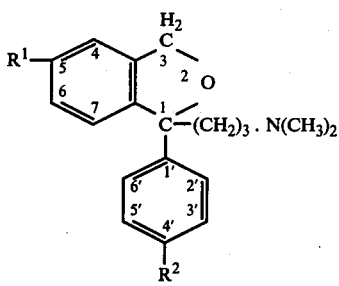

wherein $R^1$ and $R^2$ each is selected from the group consisting of halogen, a trifluoromethyl group, a cyano group and R—CO—, wherein R is an alkyl radical with from 1-4 C-atoms inclusive, and (2) an acid addition salt thereof with a pharmaceutically acceptable acid.

2. A compound according to claim 1, wherein at least one of $R^1$ and $R^2$ is a cyano group.

3. a compound according to claim 1, wherein at least one of $R^1$ and $R^2$ is R—CO—.

4. A compound according to claim 2, which is 1-(4'-fluorophenyl)-1-(3-dimethylaminopropyl)-5-phthalan-carbonitrile or an acid addition salt thereof with a pharmaceutically acceptable acid.

5. A compound according to claim 4, which is 1-(4'-fluorophenyl)-1-(3-dimethylaminopropyl)-5-phthalancarbonitrile.

6. A compound according to claim 4, which is the hydrobromide of 1-(4'-fluorophenyl)-1-(3-dimethylaminopropyl)-5-phthalancarbonitrile.

7. A compound according to claim 2, which is 1-(4'-chlorophenyl)-1-(3-dimethylaminopropyl)-5-phthalan-carbonitrile or an acid addition salt thereof with a pharmaceutically acceptable acid.

8. A compound according to claim 7, which is 1-(4'-chlorophenyl)-1-(3-dimethylaminopropyl)-5-phthalan-carbonitrile.

9. A compound according to claim 7, which is the hydrobromide of 1-(4'-chlorophenyl)-1-(3-dimethylaminopropyl)-5-phthalancarbonitrile.

10. A compound according to claim 2, which is 1-(4'-cyanophenyl)-1-(3-dimethylaminopropyl)-5-phthalan-carbonitrile or an acid addition salt thereof with a pharmaceutically acceptable acid.

11. A compound according to claim 10, which is 1-(4'-cyanophenyl)-1-(3-dimethylaminopropyl)-5-phthalancarbonitrile.

12. A compound according to claim 10, which is the hydrochloride of 1-(4'-cyanaphenyl)-1-(3-dimethylaminopropyl)-5-phthalancarbonitrile.

13. A pharmaceutical composition in unit dosage form useful in treating depression comprising a major quantity of a pharmaceutical carrier and as an active ingredient a pharmaceutically effective dose of a compound as defined in claim 1.

14. A composition according to claim 13, wherein the active ingredient is present in an amount of from 0.5 to 50 milligrams per unit dose calculated as the free amine.

15. A composition according to claim 13, wherein the active ingredient is present in an amount of from 1.1 to 25 milligrams per unit dose calculated as the free amine.

16. A composition according to claim 13, wherein the active ingredient is selected from the group consisting of 1-(4'-fluorophenyl)-1-(3-dimethylaminopropyl)-5-phthalancarbonitrile and a pharmaceutically acceptable acid addition salt thereof.

17. A method for producing an antidepressant effect in warm-blooded animals comprising administering to said warm-blooded animal an antidepressant effective amount of a compound as defined in claim 1.

18. The method of claim 17, wherein the compound administered to said warm-blooded animal is 1-(4'-fluorophenyl)-1-(3-dimethylaminopropyl)-5-phthalan-carbonitrile or a pharmaceutically acceptable acid addition salt thereof.

* * * * *

UNITED STATES PATENT AND TRADEMARK OFFICE
CERTIFICATE OF CORRECTION

PATENT NO. : 4,136,193
DATED : January 23, 1979
INVENTOR(S) : Bøgesø et al.

It is certified that error appears in the above-identified patent and that said Letters Patent are hereby corrected as shown below:

[56] References Cited, U.S. Patent Documents; "Petersen et al." should read
-- Petersen et al. (I) --

[57] Abstract, line 1; "phthalans" should read -- phthalanes --
Col. 1, line 6; "phthalans" should read -- phthalanes --
Col. 1, line 22; "phthalans" should read -- phthalanes --
Col. 1, line 23; "2,467,675" should read -- 3,467,675 --
Col. 1, line 53; "phthalans" should read -- phthalanes --
Col. 2, line 3; "phthalans" should read -- phthalanes --
Col. 2, line 5; "phthalans" should read -- phthalanes --
Col. 4, line 12; "bromophthalan" should read -- bromophthalane --
Col. 4, line 66; "bromophthalan" should read -- bromophthalane --
Col. 7, line 32; "5ionylphthalane" should read -- 5-propionylphthalane --
Col. 7, lines 38 & 39; "dimethylaminoprol" should read
-- dimethylaminopropyl --
Col. 8, line 27; "nartriptyline" should read -- nortriptyline --

Col. 10, line 20; "Scan." should read -- Scand. --
Col. 10, line 26; "$^3$H-NA washed" should read -- $^3$H-NA was washed --
Col. 11, line 21; "a" should read -- A --

Signed and Sealed this

Twenty-ninth Day of May 1979

[SEAL]

Attest:

RUTH C. MASON
Attesting Officer

DONALD W. BANNER
Commissioner of Patents and Trademarks